United States Patent [19]

Murib

[11] 4,144,398

[45] * Mar. 13, 1979

[54] PROCESS FOR THE PREPARATION OF ACROLEIN AND ACRYLIC ACID

[75] Inventor: Jawad H. Murib, Cincinnati, Ohio

[73] Assignee: National Distillers and Chemical Corporation, New York, N.Y.

[*] Notice: The portion of the term of this patent subsequent to Sep. 27, 1994, has been disclaimed.

[21] Appl. No.: 813,643

[22] Filed: Jul. 7, 1977

[51] Int. Cl.$^2$ .................... C07C 45/00; C07C 51/32
[52] U.S. Cl. ................................ 562/524; 260/549; 260/601 R
[58] Field of Search .................. 260/526 N, 601 R

[56] References Cited

U.S. PATENT DOCUMENTS

| | | | |
|---|---|---|---|
| 2,042,220 | 5/1936 | Groll et al. | 260/531 R |
| 3,778,477 | 12/1973 | Muller et al. | 260/603 R |
| 4,051,181 | 9/1977 | Murib | 260/531 R |

*Primary Examiner*—Vivian Garner
*Attorney, Agent, or Firm*—Kenneth D. Tremain

[57] ABSTRACT

Process for the preparation of acrolein, acrylic acid and mixtures thereof or methacrolein, methacrylic acid and mixtures thereof by the vapor phase reaction of allyl acetate or methallyl acetate and oxygen in the presence of a heterogeneous catalyst composition comprising a catalytically effective amount of palladium metal.

7 Claims, No Drawings

PROCESS FOR THE PREPARATION OF ACROLEIN AND ACRYLIC ACID

BACKGROUND OF THE INVENTION

The present invention relates to a process for the preparation of acrolein, acrylic acid and mixtures thereof or methacrolein, methacrylic acid and mixtures thereof by the vapor phase reaction of allyl acetate or methallyl acetate and oxygen in the presence of a heterogeneous catalyst composition comprising a catalytically effective amount of palladium metal.

Acrolein and acrylic acid and methacrolein and methacrylic acid are very important chemicals and are particularly useful in the preparation of a variety of commercial products, including plastic sheet and molding powder for signs, emulsion polymers for water-based paint formulations, paper coating, and many other such applications.

A number of processes have been proposed for the preparation of these materials and are well-known in the art. See, for example, "Encyclopedia of Chemical Technology", Second Edition, Kirk-Othmer, Vol. 1, pages 293–295. Also, Chapter 10 of "Propylene and Its Industrial Derivatives", by E. G. Handcock, published by John Wiley, New York, 1973.

U.S. Pat. No. 3,792,086 describes a process employing a catalyst composition containing phosphoric acid and palladium metal in the preparation of acrylic or methacrylic acids by the vapor phase oxidation of propylene or isobutylene, respectively. A number of U.S. patents directed to the preparation of such products are noted therein. U.S. Pat. No. 3,758,551 discloses a vapor phase process for the preparation of acrylate and methacrylate esters. U.S. Pat. No. 3,947,495 shows an improved catalyst composition containing a sulfur modifier.

British Pat. No. 1,101,056 discloses a liquid phase oxidation process for the production of esters, aldehydes, ketones and acids by reacting a material such as allyl acetate in the presence of an aliphatic carboxylic acid with oxygen in a homogeneous redox system containing a palladium salt and a salt of copper or iron and further including chloride or bromide ions. Illustrative of the reaction solution is glacial acetic acid, palladium chloride, lithium chloride, lithium acetate, cupric acetate and allyl acetate. Serious disadvantages are associated with such homogeneous catalysis as, for example, difficulty encountered in separating the reaction product from the soluble catalyst. U.S. Pat. No. 3,625,996 shows a liquid phase process for preparing olefinic acids or esters from dicarboxylic acids or esters by contacting these compounds with a complex catalyst comprising a Group VIII noble metal and a ligand of organic phosphines, arsines or stibines.

Applicant's U.S. application Ser. No. 603,907, now U.S. Pat. No. 4,051,181, issued Sept. 27, 1977 shows a step-wise vapor phase process for the oxidation of propylene to acrylic acid via allyl alcohol.

It is among the objects of the present invention to provide a new and improved process for the preparation of acrolein, acrylic acid and mixtures thereof or methacrolein, methacrylic acid and mixtures thereof from allyl acetate or methallyl acetate by a direct and efficient vapor phase process.

Other objects and advantages of the invention will be apparent from the following description.

SUMMARY OF THE INVENTION

It has now been found that acrolein, acrylic acid and mixtures thereof or methacrolein, methacrylic acid and mixtures thereof may be prepared by a direct and efficient vapor phase process comprising reacting allyl acetate or methallyl acetate and oxygen in the presence of a heterogeneous catalyst composition comprising a catalytically effective amount of palladium metal.

For convenience, the following description of the preferred forms of the invention will relate principally to the oxidation of allyl acetate to acrylic acid and acrolein. It will be understood, however, that the instant process is equally applicable to the vapor phase oxidation of methallyl acetate to methacrylic acid and methacrolein as set forth hereinabove, and that such latter embodiment is also embraced within the scope of the present invention.

The process is generally carried out at elevated temperatures, e.g., up to about 300° C., employing a heterogeneous catalyst contact system, such as a system utilizing a fixed, moving or fluidized catalyst bed.

It has been found unexpectedly that using the method of the invention, the oxygen attack on the allyl acetate is preferentially directed to the allylic carbon of said material and results in preferential conversion to acrolein and acrylic acid with only a minimum of side reactions forming minor amounts of materials such as acetaldehyde, propionaldehyde and carbon dioxide. While not wishing to be bound by any theory as to the mechanism of the reaction, it is hypothesized that the allyl acetate is preferentially oxidized at the allylic carbon atom because of activation by its allylic position and its linkage to the ester group. The oxidation is assumed to form the mixed acrylic-acetic anhydride and water. Subsequent hydrolysis of the anhydride in situ leads to acrylic acid and acetic acid. The latter can be recycled to form allyl acetate by reaction with propylene and oxygen according to known art.

DESCRIPTION OF THE PREFERRED EMBODIMENTS

The allyl acetate reacted in the present process may be used in pure form or in diluted form, such as, for example, in the form of a mixture containing up to about 50 mole percent of diluents, usually inert hydrocarbons, e.g., heptane, hexane, cyclohexane and benzene.

The oxygen feed may similarly be pure oxygen gas or, alternatively, an oxygen-containing gas mixture such as air or air enriched with oxygen. In addition to these materials the oxygen may contain other inert diluents such as carbon dioxide, nitrogen, and the like.

The amount of oxygen employed is not excessively critical. Thus, stoichiometric proportions of oxygen, i.e., one-half mole of oxygen per one mole of allyl acetate, can be used. In general, the mole ratio of oxygen to allyl acetate can be about 10:1 to 1:10, preferably 5:1 to 1:5, and is, most preferably, about 2:1 to 1:2, e.g., 0.58:1. Obviously, when inert diluents are present in the reaction mixture, e.g., when the oxygen is added in the form of air, the proportions of the several reactants are correspondingly modified.

The catalyst composition comprises a catalytically effective amount of palladium metal, suitably supported on a conventional catalyst carrier such as, for example, alumina, silica, active carbon, silicon carbide, carbon graphite, titania, zirconia, zeolites, and the like. Active carbon and silica are preferably utilized as the catalyst carrier in the process hereof because of superior stability and surface area, activity characteristics, among others.

The catalyst particle size, e.g., silica carrier, can vary over wide limits, e.g., about 0.5 to 10 millimeter (mm.) average diameter, preferably 0.5 to 5 mm., and generally has a specific surface area of about 50 to 2000 square meters per gram ($m^2/g$) and is preferably about 500 to 1000 $m^2/g$. The preferred active carbon (sold by Westvaco as Nuchar active carbon—Grade WV-L 8X30) has an effective particle size of about 0.9 mm., with a range of about 8 mesh to 30 mesh, U.S. Sieve Series, and a specific surface area of about 1000 $m^2/g$.

The catalyst composition may be prepared by known techniques. Thus, for example, the catalyst may be prepared by spraying, applying solutions or otherwise depositing on the support a solution containing a palladium salt, evaporating the solvent and reducing the salt with an appropriate reagent, e.g., hydrogen, alkaline formaldehyde, hydrazine or alkali metal borohydride. The palladium metal deposited upon the carrier is generally, by weight of the total catalyst composition, about 0.01 to 5%, preferably about 0.1 to 2%, e.g., about 1.25%.

The catalyst composition may also preferably contain, in the metallic state, copper, silver or gold or mixtures thereof. The total amount of these metals, by weight of the total catalyst composition, will generally be about 0.1 to 3%, e.g., 2% and preferably about 0.5 to 1.5%. As with the preparation of the catalyst containing palladium metal described hereinabove, these metals may also be deposited on the catalyst carrier by similarly conventional techniques and in any desired sequence. A catalyst composition containing about 1.25% palladium metal and 0.55% gold metal supported on Nuchar active carbon has been found to be particularly effective.

This reaction is conducted in the vapor phase and is relatively simple and efficient since no moving parts are required in the processing equipment. Product separation is simplified and the reaction product can be separated from the reaction mixture by techniques such as distillation or solvent extraction. Further, vapor phase reactions generally permit continuous operation and do not necessitate the use of expensive, volatile solvents, as in liquid phase systems.

In carrying out the process, it may be conducted either at atmospheric or elevated pressures, e.g., up to about 300 pounds per square inch gauge (psig), or higher. It is generally preferred to carry out the process under atmospheric pressure or at pressures only slightly in excess of atmospheric, e.g., up to about 50 psig, and most preferably up to about 20 or 30 psig, e.g., 10 psig.

The reaction temperature employed in the process may be varied over a relatively wide range and, for example, temperatures of as high as about 300° Centigrade (° C.), and above, are suitable. It is preferred to maintain the reaction temperature at about 150°-250° C., and most preferably about 150°-200° C. In general, the contact time of the reaction stream with the catalyst will vary inversely with the reaction temperature, i.e., it being possible to use higher reaction temperatures when employing shorter contact times and, conversely, lower reaction temperatures at longer contact times. At the preferred reaction temperature range of about 150°-250° C., a contact time of about 0.1 to 20 seconds, preferably 1 to 10 seconds, provides excellent results.

After the gaseous reaction mixture contacts the catalyst composition, the exhaust gases are cooled and the products separated by conventional techniques, e.g., distillation, solvent extraction, and the like. Unreacted feed material separated from the recovered effluent mixture may thereafter be recovered and recycled for further reaction.

An important feature of the invention is an improved multi-step process for the preparation of acrolein and acrylic acid from propylene. As described in U.S. Pat. Nos. 3,190,912 and 3,275,680, said patents being incorporated herein by reference, allyl acetate may be prepared by reacting propylene, oxygen and acetic acid in the presence of a noble metal catalyst (Step 1). In accordance with this aspect of the invention, the allyl acetate thus produced in Step 1 would be the feed material to produce the acrolein and acrylic acid in accordance with the invention.

Acetic acid produced as a by-product of the allyl acetate oxidation, may be recycled to Step 1 to prepare the allyl acetate from propylene. This two-step procedure provides an efficient and effective process for the preparation of acrolein and acrylic acid from propylene. The total reaction product from Step 1 may be used as the feed stream to produce the acrolein and acrylic acid in accordance with the invention, although this is not preferred.

A similar procedure may be employed using methallyl acetate to form methacrolein and methacrylic acid.

The following examples are given for purposes of illustration only and are not to be considered as constituting a limitation on the present invention. In the examples, all parts and percentages are given by weight and temperatures in degrees Centigrade unless otherwise specified.

EXAMPLE I

A Pyrex glass reactor 12 centimeter (cm.) × 2.5 cm. outside diameter (O.D.) was provided with a thermowell (0.8 cm. O.D.) extending the entire length of the reactor and is attached to a preheating zone (1.2 × 15 cm.) and a capillary exit tube (0.1 × 10 cm.) to permit rapid quenching. The reactor was packed with 15 grams (g.) [30 milliliters (ml) bulk volume] of a catalyst containing 1.25% Pd metal and 0.55% Au metal supported on Nuchar active carbon (Grade WV-L 8X30). The reaction was heated in an oil bath maintained at 152° C.

A gaseous stream of 26.5 mole % allyl acetate and 73.5 mole % air (mole ratio of oxygen to allyl acetate is about 0.58) was passed through the heated catalyst bed at atmospheric pressure and about 5.1 seconds contact time. The exhaust reaction gases were condensed by passing through a U-tube maintained at about 0° C. Analysis of the condensate by mass spectroscopy and vapor phase chromatography showed preferential formation of acrolein, acrylic acid and acetic acid and minor amounts of acetaldehyde, propionaldehyde and carbon dioxide.

EXAMPLE II

Example I is repeated except that the catalyst support is (1) alumina and (2) silica.

EXAMPLE III

Example I is repeated except that the catalyst contains copper instead of gold.

EXAMPLE IV

Example I is repeated except that (1) gold is replaced by silver and (2) only palladium metal is employed as the catalyst.

EXAMPLE V

Example I is repeated substituting methallyl acetate for the allyl acetate.

While the invention has been directed to allyl acetate and acrolein and acrylic acid and to methallyl acetate and methacrolein and methacrylic acid, it will be understood that the disclosed process is applicable to the preparation of other corresponding aldehydes, carboxylic acids and mixtures thereof from esters having an allylic carbon atom and that such other embodiments are, therefore, also embraced within the scope of the present invention. For example, methallyl propionate, allyl butyrate, crotyl acetate, and the like, may be employed.

It will be apparent that many changes and modifications of the several features described herein may be made without departing from the spirit and scope of the invention. It is therefore apparent that the foregoing description is by way of illustration of the invention rather than limitation of the invention.

I claim:

1. A vapor phase process for the preparation of acrolein, acrylic acid and mixtures thereof or methacrolein, methacrylic acid and mixtures thereof which comprises reacting allyl acetate or methallyl acetate and oxygen in the presence oof a heterogeneous catalyst composition consisting essentially of a catalytically effective amount of palladium metal or palladium metal and a metal selected from the group consisting of copper, silver and gold and mixtures thereof.

2. A process as in claim 1 wherein the molar ratio of oxygen to allyl acetate is about 10:1 to 1:10 and the catalyst is palladium metal.

3. A process as in claim 1 wherein the process is at a temperature up to about 300° C. and a pressure of about atmospheric to 300 psig.

4. A process as in claim 3 wherein the palladium is in an amount, by weight of the total catalyst composition, of about 0.01% to 5%.

5. A process as in claim 1 wherein the catalyst composition is palladium metal and a metal selected from the group consisting of copper, silver, gold and mixtures thereof and wherein, by weight of the total catalyst composition, the palladium metal is about 0.01% to 5% and the total amount of copper, silver and gold is about 0.1% to 3%.

6. A process as in claim 5 wherein the temperature is in the range of about 150°–200° C. and the pressure is about atmospheric to 10 psig.

7. A process as in claim 6 wherein the amount of palladium is about 0.1 to 2%, the catalyst contains gold in an amount of about 0.5 to 1.5%, and the catalyst composition is supported on active carbon.

* * * * *